US008591106B2

United States Patent
Nishino et al.

(10) Patent No.: US 8,591,106 B2
(45) Date of Patent: Nov. 26, 2013

(54) RADIOGRAPHIC IMAGE CAPTURE SYSTEM, PORTABLE RADIOGRAPHIC IMAGE CAPTURE DEVICE, IMAGE CAPTURE TABLE

(75) Inventors: Naoyuki Nishino, Kanagawa (JP); Yasunori Ohta, Kanagawa (JP); Futoshi Yoshida, Kanagawa (JP); Naoto Iwakiri, Kanagawa (JP); Haruyasu Nakatsugawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 261 days.

(21) Appl. No.: 13/104,041

(22) Filed: May 10, 2011

(65) Prior Publication Data

US 2011/0280369 A1 Nov. 17, 2011

(30) Foreign Application Priority Data

May 12, 2010 (JP) .................................. 2010-110540

(51) Int. Cl.
*H01J 31/49* (2006.01)

(52) U.S. Cl.
USPC ........................................................ 378/189

(58) Field of Classification Search
USPC ................................................. 378/189, 190
See application file for complete search history.

(56) References Cited

U.S. PATENT DOCUMENTS 7,988,356 B2 * 8/2011 Watanabe ..................... 378/189

FOREIGN PATENT DOCUMENTS

| JP | 2002-006049 | | 1/2002 |
| JP | 2005-181922 | A | 7/2005 |
| JP | 2007-222604 | A | 9/2007 |
| JP | 2008-36399 | A | 2/2008 |
| JP | 2009-28234 | A | 2/2009 |
| JP | 2009-288196 | * | 10/2009 |

OTHER PUBLICATIONS

English language translation of the following: Office action dated Sep. 10, 2013 from the JPO in a Japanese patent application corresponding to the instant patent application. This office action translation is submitted now in order to supplement the understanding of patent document JP2002-006049 which is cited in the office action and is being disclosed in the instant Information Disclosure Statement.

* cited by examiner

*Primary Examiner* — Jurie Yun
(74) *Attorney, Agent, or Firm* — SOLARIS Intellectual Property Group, PLLC (57) ABSTRACT

An inflow port is provided to a casing of an electronic cassette in order to pass air from outside through the inside of electronic cassette. Air is flowed to the inflow port when the electric cassette is housed in a housing section of a prone image capture table. Efficient cooling can accordingly be achieved with a simply configured portable radiographic image capture device.

8 Claims, 8 Drawing Sheets

RADIOGRAPHIC IMAGE CAPTURE SYSTEM, PORTABLE RADIOGRAPHIC IMAGE CAPTURE DEVICE, IMAGE CAPTURE TABLE

CROSS-REFERENCE TO RELATED APPLICATION

This application claims priority under 35 USC 119 from Japanese Patent Application No. 2010-110540 filed on May 12, 2010, the disclosure of which is incorporated by reference herein.

BACKGROUND

1. Technical Field

The present invention relates to a radiographic image capture system, a portable radiographic image capture device, and an image capture table.

2. Related Art

Recently, radiation detectors have been put into practice employing, for example, a FPD (Flat Panel Detector) that has a radiation sensitive layer disposed on a TFT (Thin Film Transistor) active matrix substrate, detects irradiated radiation, such as X-rays, and outputs electrical signals expressing radiographic images representing the detected radiation. Such radiation detectors have the advantage that, in comparison to conventional imaging plates, images can be more immediately checked and video images can also be checked.

Portable radiographic image capture devices (referred to below as electronic cassettes) installed with radiation detectors such as these for capturing radiographic images are being put into practice.

It is desirable for such electronic cassettes to be smaller, lighter and thinner, due to their mode of use. In consideration of use, such as during doctor's rounds and with dusty beds, there is also desirable for the electronic cassettes to be closely sealed.

Electronic cassettes are capable of capturing video images (fluoroscopic imaging) by performing successive capture with the radiation detectors, however, heat presents a problem when the electronic cassettes are closely sealed, due to the heat generated by image capture from electronic circuits inside the electronic cassettes.

As techniques to address this issue, techniques are described in Japanese Patent Application Laid-Open (JP-A) Nos. 2007-222604, 2008-36399 and 2009-28234 in which heat dissipation is performed when an electronic cassette is set in an image capture table by contacting the casing of the electronic cassette to a cooling mechanism.

There is also a technique described in JP-A No. 2005-181922 in which a cooling unit that suppresses temperature rise inside a casing is embedded within the casing of an electronic cassette, so as to be installable or removable.

However, there are occasions that sufficient cooling of the electronic cassette cannot be achieved by performing heat dissipation using the techniques of JP-A Nos. 2007-222604, 2008-36399 and 2009-28234 in which the casing of the electronic cassette is caused to contact a cooling mechanism.

In particular, the internal temperature of an electronic cassette readily rises when performing fluoroscopic imaging, since successive image capture is performed by the radiation detector.

Whilst sufficient cooling of the electronic cassette can be achieved when a cooling unit is embedded so as to be install- able and removable with the technique of JP-A No. 2005-181922, effort is required to change over the cooling unit.

SUMMARY

The present invention is made in consideration of the above circumstances and provides a radiographic image capture system, a portable radiographic image capture device, and an image capture table capable of efficiently cooling a portable radiographic image capture device with a simple configuration.

A radiographic image capture system of a first aspect of the present invention includes: a portable radiographic image capture device including a sensor section that is sensitive to radiation or to light converted from radiation, an electronic circuit that controls capture of a radiographic image by the sensor section, and a casing that houses the sensor section and the electronic circuit and is provided with a flow port for flowing a cooling medium through from outside to inside; and an image capture table including a housing section that houses the portable radiographic image capture device, and an inflow mechanism that flows the cooling medium into the flow port of the portable radiographic image capture device when housed in the housing section.

BRIEF DESCRIPTION OF THE DRAWINGS

Exemplary embodiments of the present invention will be described in detail based on the following figures, wherein.

DETAILED DESCRIPTION

Explanation now follows regarding an exemplary embodiment for realizing the present invention, with reference to the drawings.

Figure 1:
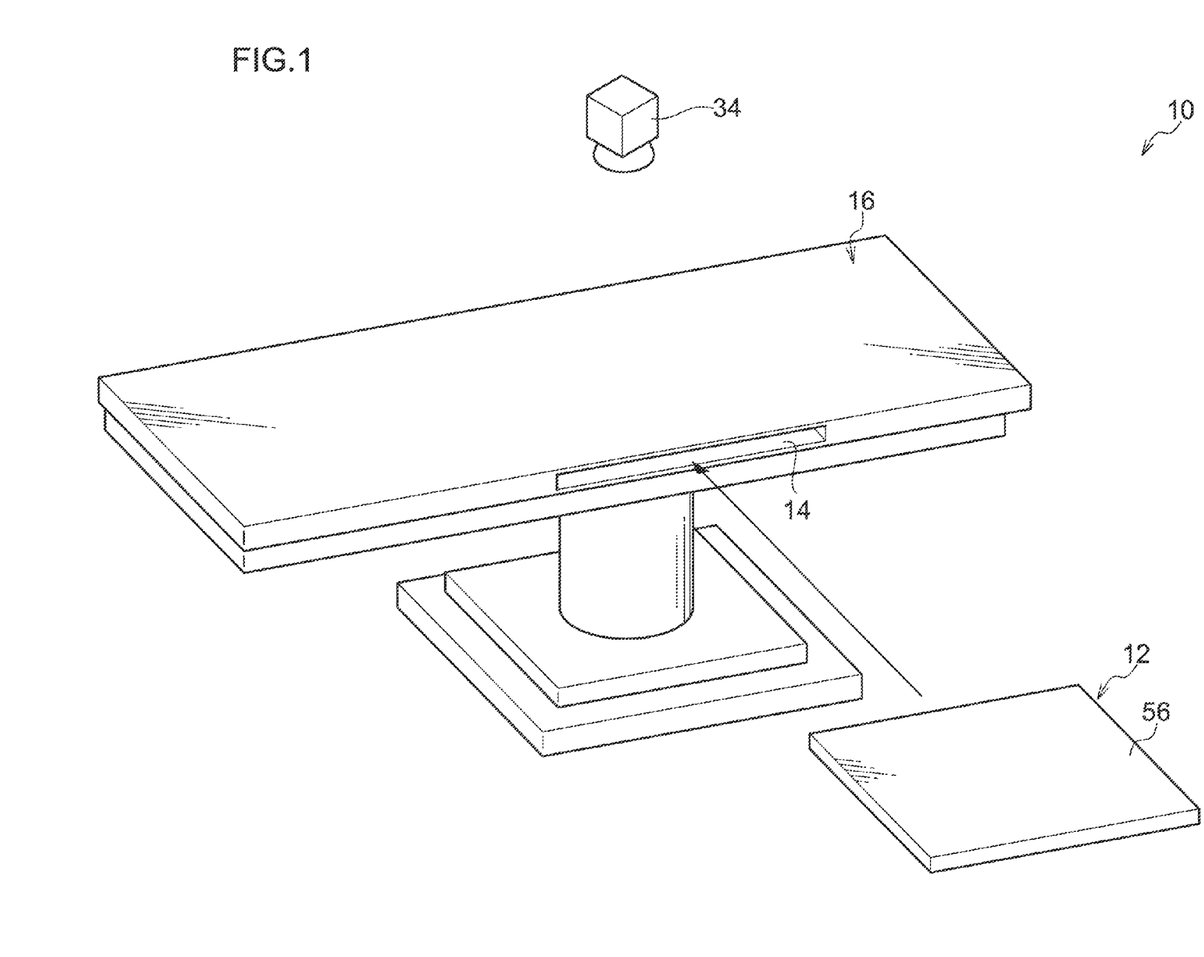
FIG. 1 is a perspective view of a configuration of a radiographic image capture system according to an exemplary embodiment of the present invention.

A radiographic image capture system 10 according to an exemplary embodiment is illustrated in FIG. 1.

The radiographic image capture system 10 includes: a portable electronic cassette 12 that generates image data each time radiation carrying image information is irradiated and is capable of accumulating and storing the generated image data; and a prone image capture table 16 for a patient to lie down on when radiographic image capture in a prone position is performed, the prone image capture table 16 being provided with a housing section 14 for housing the electronic cassette 12.

The electronic cassette 12 is disposed with a separation to a radiation generation device 34 by housing the electronic cassette 12 in the housing section 14 of the prone image capture table 16. There is an image capture position for positioning a patient, between the radiation generation device 34 and the electronic cassette 12. When radiographic image capture is instructed, the radiation generation device 34 irradiates X-rays with a radiation dose in accordance with pre-instructed image capture conditions or the like. The X-rays emitted from the radiation generation device 34 pass through the patient positioned at the image capture position, and are then irradiated onto the electronic cassette 12 after picking up image information.

Figure 2:
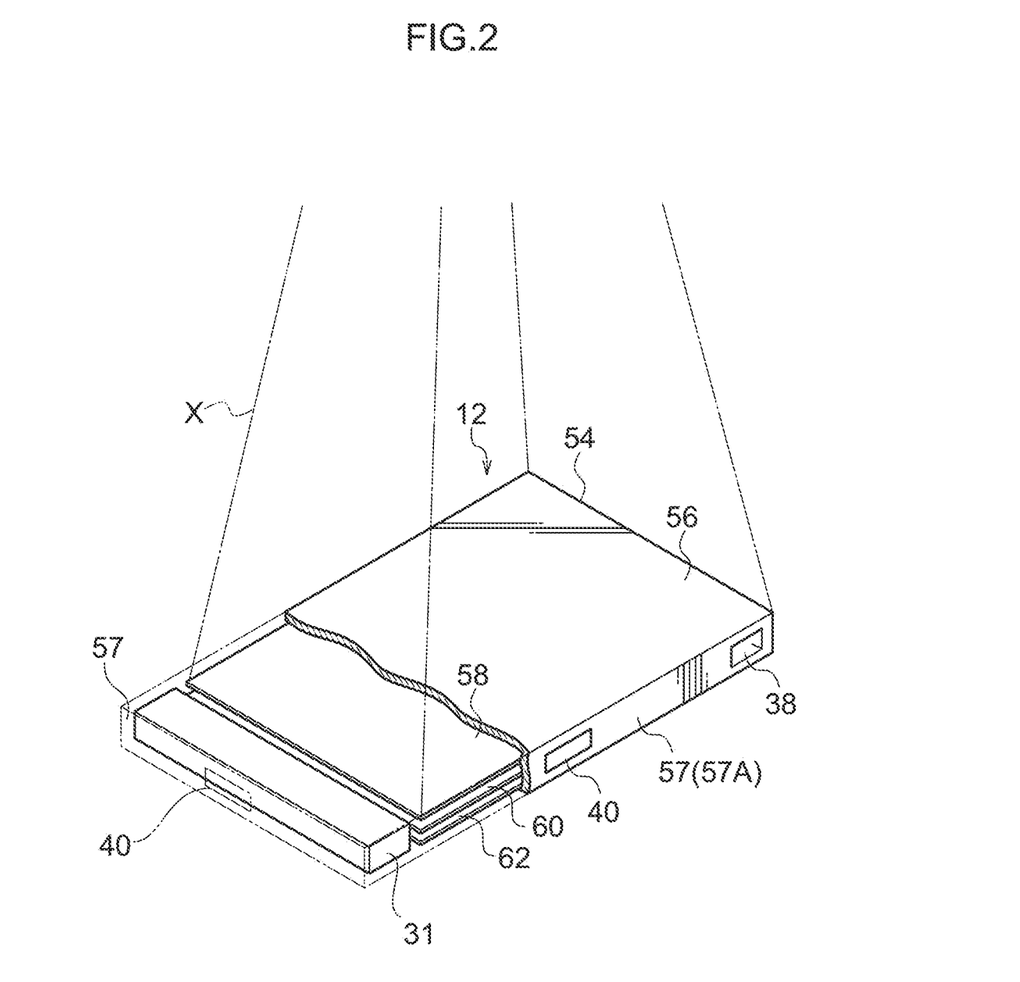
FIG. 2 is a cutaway perspective view showing an internal configuration of an electronic cassette according to an exemplary embodiment of the present invention.

FIG. 2 illustrates an internal configuration of the electronic cassette 12 according to the present exemplary embodiment.

As shown in FIG. 2, the electronic cassette 12 includes a casing body 54 formed from a material that lets X-rays pass through, and has a waterproof and tightly sealed construction. Occasions might arise when blood fluids or other germ containing substances adhere to the electronic cassette 12, such as when being used in an operating theater. Accordingly, by constructing the electronic cassette 12 so as to be waterproof and tightly sealed, a single electronic cassette 12 can be reused repeatedly by sterilization and cleaning as required.

Disposed inside the casing body 54 are, in sequence from the X-ray-irradiated irradiation face 56 side of the casing body 54, a grid 58 for removing X-rays scattered by the patient, a radiation detector 60 for detecting X-rays that have passed through the patient, and a lead plate 62 for absorbing backscattered X-rays. Note that the irradiation face 56 of the casing body 54 may also be configured by the grid 58.

A case 31 for housing electronic circuits including a microcomputer and a rechargeable battery is disposed inside the casing body 54 at one end. The radiation detector 60 and the electronic circuits are operated by power supplied from the rechargeable battery disposed in the case 31. Preferably a lead plate or similar member is disposed on the irradiation face 56 side of the case 31 in order to avoid damage accompanying irradiation of X-rays to the various circuits housed in the case 31. The electronic cassette 12 according to the present exemplary embodiment is a rectangular box shape with a rectangular shaped irradiation face 56, with the case 31 disposed at one length direction end of the electronic cassette 12.

The electronic cassette 12 is provided with a flow port 38 in one side face 57A of the casing body 54 to let air, serving as a cooling medium, pass through from outside to inside the electronic cassette 12.

Figure 3:
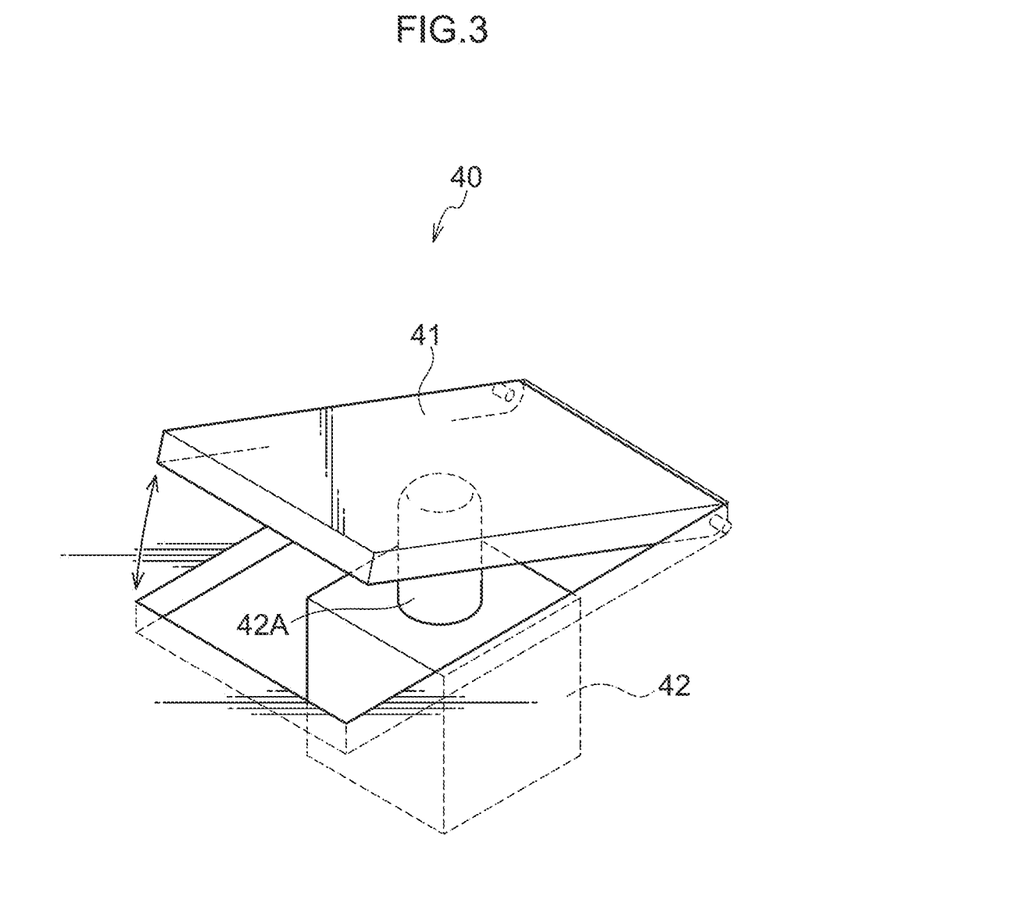
FIG. 3 is an enlarged perspective view of an enlarged air passage port according to an exemplary embodiment of the present invention.

An air passage port 40 is provided at each of the side faces 57 to let air pass through. Provided at each of the air passage ports 40 are, as shown in FIG. 3, a lid member 41, and an opening and closing mechanism 42 for closing or opening each of the air passage ports 40 using the lid member 41. Each of the opening and closing mechanisms 42 includes a rod 42A, connected to the lid member 41 and capable of extending and retracting. The rod 42A is extended by movement force of an internally housed actuator, opening the air passage port 40 by pressing the lid member 41. The air passage port 40 is closed by contracting the rod 42A and placing the lid member 41 in a closely sealed state over the air passage port 40. Note that the inside of the casing body 54 is configured with a light blocking structure such that light entering through the air passage port 40 is blocked even when each of the air passage ports 40 is open, thereby preventing light entering from the air passage ports 40 from being incident to the radiation detector 60.

Figure 4:
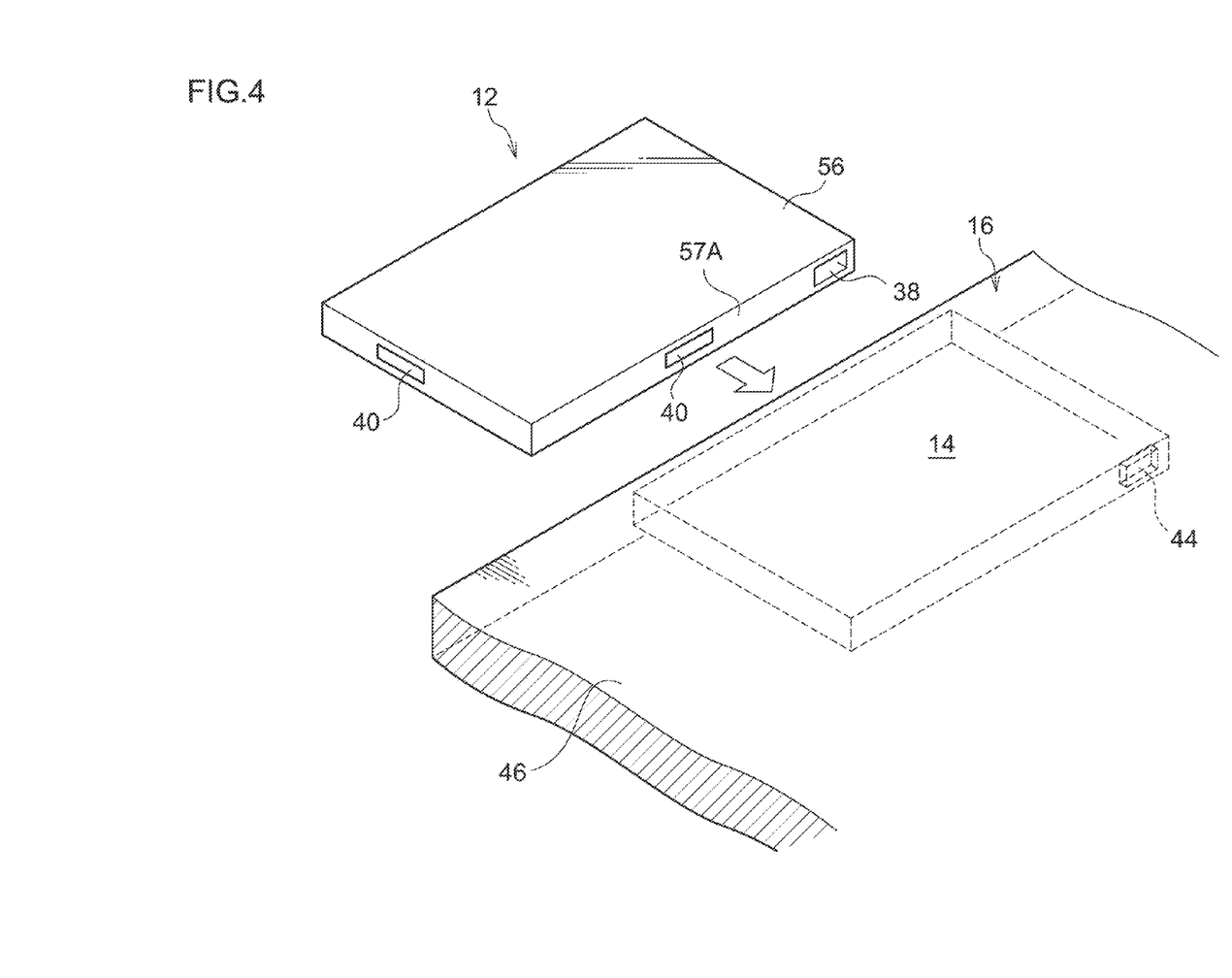
FIG. 4 is a cutaway perspective view showing a configuration of a housing section according to an exemplary embodiment of the present invention.

The electronic cassette 12, as shown in FIG. 4, is housed in a housing section 14, with the side face 57A foremost. A supply port 44 for air supply is provided at a position in the housing section 14 so as to be aligned with the flow port 38 when the electronic cassette 12 is in a housed state in the housing section 14. A non-return valve is provided to the flow port 38 of the electronic cassette 12, such that air is able to flow through when the flow port 38 is connected to the supply port 44. Contact detection sensors 46, 47 (see FIG. 5 and FIG. 6), for example mechanical switches, are provided to the flow port 38 and the supply port 44, respectively, for detecting whether or not the flow port 38 and the supply port 44 are connected together, enabling detection of the connection state to the supply port 44.

Figure 5:
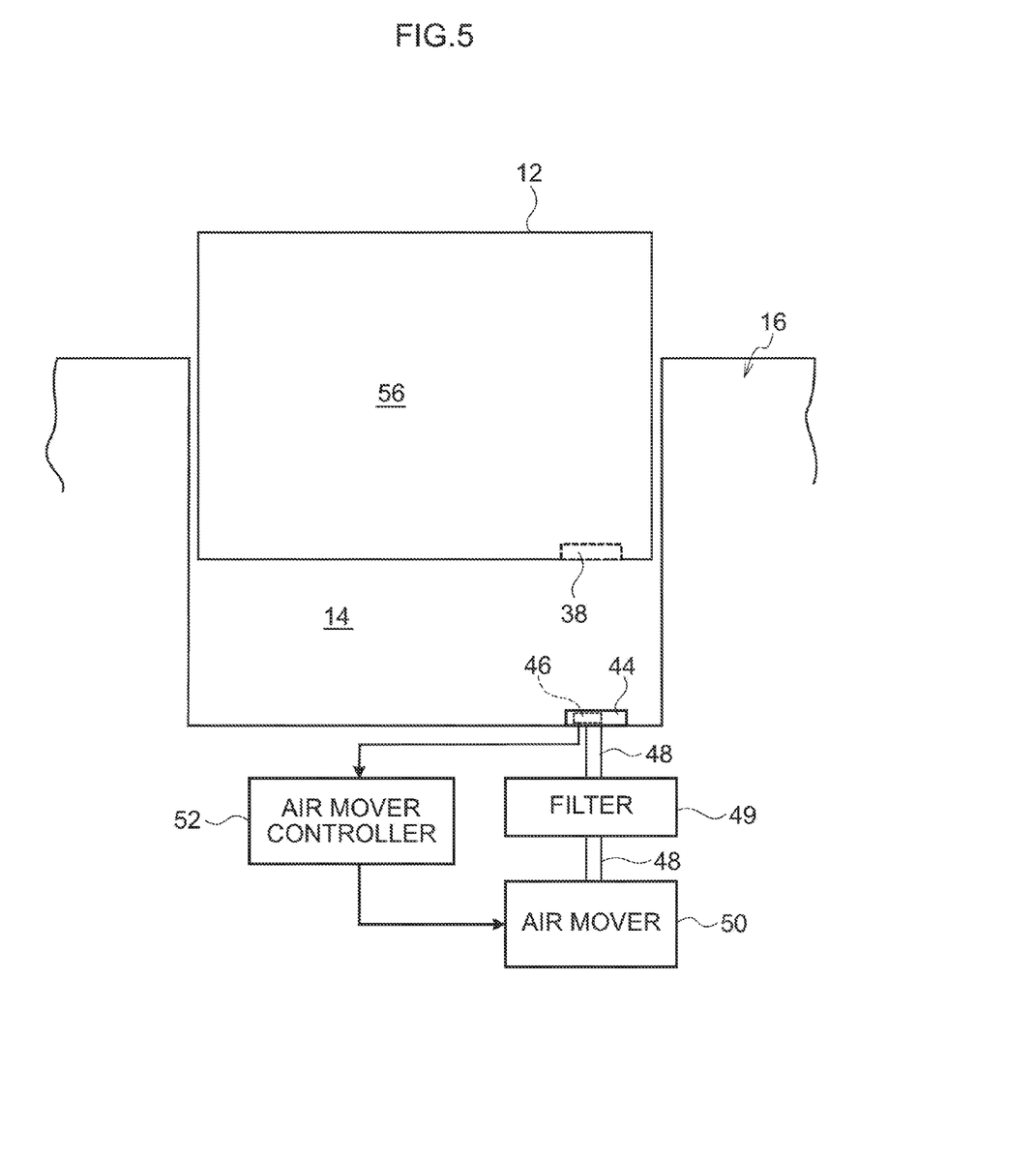
FIG. 5 is a cross-section view showing a configuration of an electronic cassette and a housing section according to an exemplary embodiment of the present invention.

As shown in FIG. 5, the supply port 44 is connected to an air mover 50 through a duct 48, and air dispatched from the air mover 50 is discharged from the supply port 44. In the present exemplary embodiment a filter 49 is provided to the duct 48, and incorporated foreign objects are removed by the filter 49. Accordingly, such provision of the filter 49 can suppress dust and the like from building up inside the electronic cassette 12 and lowering the rate of heat dissipation. Problems with the electrical circuits in the electronic cassette 12 associated with such dust can also be suppressed from occurring.

The air mover 50 is connected to an air mover controller 52, configured by a microcomputer for controlling operation of the air mover 50.

The contact detection sensor 46 is connected to the air mover controller 52. The air mover controller 52 ascertains whether or not the supply port 44 is connected to the flow port 38 based on the detection result from the contact detection sensor 46, and controls the air mover 50 to start supply of air from the supply port 44 when the flow port 38 and the supply port 44 are connected together.

Figure 6:
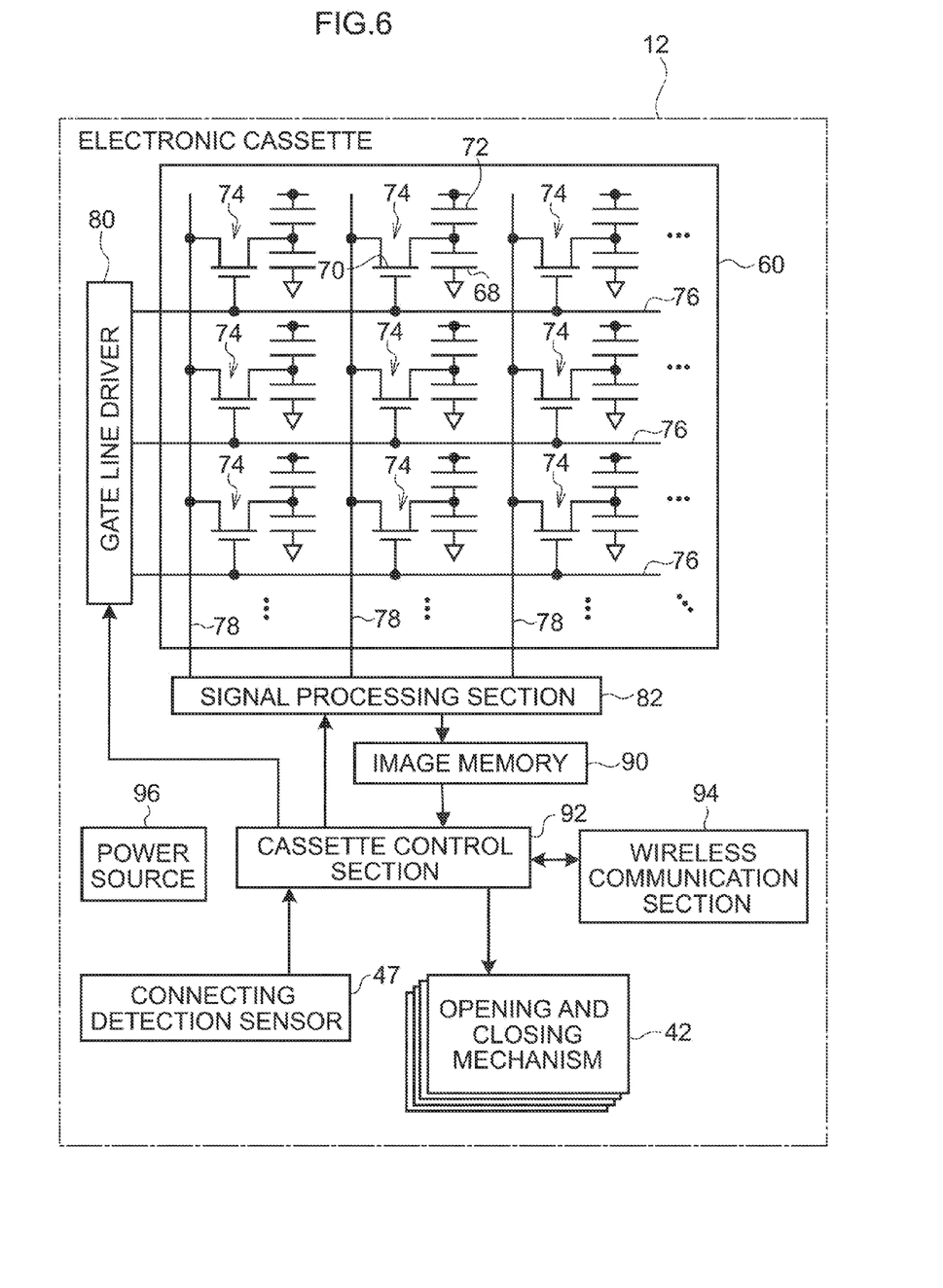
FIG. 6 is a block diagram showing a configuration of an electronic cassette according to an exemplary embodiment of the present invention.

FIG. 6 is a block diagram illustrating relevant portions of an electrical system of the electronic cassette 12 according to the present exemplary embodiment.

The radiation detector 60 is installed as a sensor section in the electronic cassette 12, and is sensitive to radiation or to light converted from radiation.

The radiation detector 60 is configured with a photoelectric conversion layer for absorbing X-rays and converting the X-rays into charge, layered on an TFT active matrix substrate 66. The photoelectric conversion layer is formed with, for example, selenium as a main component thereof (for example contained at a proportion of 50% or above) using non-crystalline a-Se (amorphous selenium). When X-rays are irradiated onto the photoelectric conversion layer, the photoelectric conversion layer converts irradiated X-rays into charge by internally generating charge (electron-hole pairs) of an amount of electric charge in accordance with the amount of irradiated radiation. It should be noted that configuration may be made such that there is indirect conversion into charge in the radiation detector 60 using a fluorescent material and photoelectric conversion element (photodiode), in place of the direct radiation-charge converting materials like amorphous selenium that directly convert X-rays into charge. Gadolinium oxysulfide compounds (GOS) and cesium iodide (CsI) are well known as fluorescent materials. In such cases X-ray-to-light conversion is performed by the fluorescent material and light-to-charge conversion is performed using the photodiode photoelectric conversion element.

Plural individual pixel portions 74 are disposed in a matrix shape on the TFT active matrix substrate 66. Each of the pixel portions 74 is provided with a storage capacitor 68 for accumulating charge generated in the photoelectric conversion layer, and a TFT 70 for reading out the charge accumulated in the storage capacitor 68 (in FIG. 6 an photoelectric conversion layer corresponding to individual pixel portions 74 is shown pictorially as photoelectric conversion portions 72). The charge generated in the photoelectric conversion layer, by irradiation of the electronic cassette 12 with X-rays, is accumulated in the respective storage capacitors 68 of the individual pixel portions 74. The image information carried by the X-rays irradiated onto the electronic cassette 12 is accordingly converted into charge data, and held in the radiation detector 60.

The TFT active matrix substrate 66 is provided with plural gate lines 76 extending along a fixed direction (row direction) for switching the TFT 70 of the individual pixel portions 74 on and off, and is provided with plural data lines 78 extending in a direction (column direction) perpendicular to the gate lines 76 for reading out accumulated charge from the storage capacitors 68 through the TFTs 70 that are switched on. Individual gate lines 76 are connected to a gate line driver 80, and individual data lines 78 are connected to a signal processing section 82. When charge has accumulated in the storage capacitor 68 of the individual pixel portions 74, the TFTs 70 of the individual pixel portions 74 are switched on in sequence of single row units by a signal supplied from the gate line driver 80 through the gate lines 76. The charge that has been accumulated in the storage capacitor 68 of the pixel portions 74 for which the TFT 70 is on, is transmitted as an analogue electrical signal through the data lines 78 and input to the signal processing section 82. The charge that has been accumulated in the storage capacitors 68 of individual pixel portions 74 is consequently read out in sequence in single row units.

Whilst not shown in the drawings, the processing section 82 is provided with an amplifier and a sample and hold circuit for each of the individual data lines 78. The charge signals transmitted by the individual data lines 78 are held in the respective sample and hold circuits after application by the respective amplifiers. A multiplexer and an analogue-digital (A/D) converter are connected in sequence to the output side of the sample and hold circuits, and the charge signals held by the individual sample and hold circuits are input in sequence (serially) to the multiplexer, and converted into digital image data by the A/D converter.

An image memory 90 is connected to the signal processing section 82. Image data output from the A/D converter of the signal processing section 82 is stored in sequence in the image memory 90. The image memory 90 has a capacity capable of storing a specific number of frames worth of image data, and each time a radiographic image is captured, the image data obtained by capture is stored in sequence in the image memory 90.

The image memory 90 is connected to a cassette control section 92 that controls the overall operation of the electronic cassette 12. The cassette control section 92 is configured by a microcomputer, and includes a Central Processor Unit (CPU), ROM, and RAM, and a non-volatile storage section configured from flash memory or the like.

A wireless communication section 94 is connected to the cassette control section 92. The wireless communication section 94 is capable of communication with a console for controlling radiographic image capture, not shown in the drawings. The cassette control section 92 controls transmission of various data to and from the console via the wireless communication section 94. The cassette control section 92 stores radiation exposure conditions, described later, received from the console via the wireless communication section 94, and commences reading out the charge based on the radiation exposure conditions.

The opening and closing mechanism 42 and the connecting detection sensor 47 are also connected to the cassette control section 92. The cassette control section 92 ascertains whether or not the supply port 44 is connected to the flow port 38 based on the detection result of the connecting detection sensor 47, and can open or close each of the air passage ports 40 by controlling the opening and closing mechanism 42 and extending or retracting the rods 42A. When the flow port 38 and the supply port 44 are not yet connected together, the cassette control section 92 controls the opening and closing mechanism 42 such that the rods 42A are retracted and both the air passage ports 40 are closed. However, when the flow port 38 and the supply port 44 are connected together, the cassette control section 92 controls the opening and closing mechanism 42 such that the rods 42A are extended, opening both the air passage ports 40.

A power source 96 is provided to the electronic cassette 12, and power supplied from the power source 96 operates the various circuits and elements described above (the gate line driver 80, the signal processing section 82, the image memory 90, the wireless communication section 94, the microcomputer functioning as the cassette control section 92, the opening and closing mechanism 42 and the connecting detection sensor 47). The power source 96 is installed with a battery (a rechargeable battery) so that the portability of the electronic cassette 12 is not compromised, and power is supplied from the charged battery to various circuits and elements. Note that the lines connecting the various circuits and various elements to the power source 96 are omitted in FIG. 6.

Explanation now follows regarding operation of the radiographic image capture system 10 according to the present exemplary embodiment.

When the electronic cassette 12 is not yet in a housed state in the housing section 14 of the prone image capture table 16, the electronic cassette 12 closes both the air passage ports 40 so as to maintain the inside of the electronic cassette 12 in a closely sealed state.

The electronic cassette 12 is inserted into the housing section 14 of the prone image capture table 16 for a doctor or radiographer to capture an image of a prone patient. The flow port 38 and the supply port 44 become connected together when the electronic cassette 12 has been housed in the housing section 14.

When the electronic cassette 12 is housed in the housing section 14 of the prone image capture table 16 and the flow port 38 and the supply port 44 are connected together, the electronic cassette 12 opens both the air passage ports 40 to enable air to flow through. The prone image capture table 16 supplies air from the supply port 44 through the flow port 38 when the flow port 38 of the electronic cassette 12 is connected to the supply port 44.

During image capture, radiation is irradiated from the radiation generation device 34 in synchronization with the timing of image capture. The radiation irradiated from the radiation generation device 34 arrives at the electronic cassette 12 after passing through the subject.

Charge is thereby accumulated in the storage capacitor 68 of each of the pixel portions 74 of the radiation detector 60, in an amount according to the irradiated radiation.

The cassette control section 92 outputs an instruction signal, to the gate line driver 80 and the signal processing section 82 instructing the start of image read out, at a timing in synchronization with image capture. When start of image reading has been instructed, an ON signal (+10 to 20V) is output from the gate line driver 80 in sequence one line at a time to each of the gate lines 76, and the TFTs 36 connected to each of the gate lines 76 are switched ON in sequence one line at a time. A charge signal according to the amount of charge that has accumulated in each of the storage capacitors 68 of the respective pixel portions 74 thereby flows as an electrical signal out through each of the data lines 78 in sequence one line at a time. The charge signal is held in the respective sample and hold circuit after amplification by the amplifier. The processing section 82 detects, as pixel values of each pixel configuring an image, the charge amount accumulated in each of the pixel portions 74 based on the charge signals flowing out in the data lines 78. Image data expressing radiographic images representing the radiation irradiated on the electronic cassette 12 can thereby be obtained. The image data obtained by image capture is stored in the image memory 90.

However, heat is generated during read out of charge accumulated in the storage capacitor 68 of each of the pixel portions 74 to obtain image data representing a radiographic image, such as by the gate line driver 80, the signal processing section 82, and the image memory 90. The temperature inside the electronic cassette 12 readily rises during fluoroscopic imaging in particular, due to successive image capture being performed.

However, in the radiographic image capture system 10 according to the present invention, since the electronic cassette 12 can be cooled by passing air through the inside of the electronic cassette 12, deterioration in image quality due to being affected by heat can be suppressed from occurring.

According to the present exemplary embodiment as described above, the flow port 38 is provided in order to pass air from outside to the inside of the casing body 54 of the electronic cassette 12, and efficient cooling of the electronic cassette 12 can be performed with a simple structure of electronic cassette 12 by passing air through the flow port 38 when the housing section 14 is housed in the prone image capture table 16.

Explanation in the above exemplary embodiment is of a case in which a cooling mechanism is provided for cooling the electronic cassette 12 housed in the housing section 14 of the prone image capture table 16, however there is no limitation thereto. For example, when an upright image capture table or another image capture table, such as a mammography image capture table, has a housing section for housing the electronic cassette 12, the cooling mechanism for cooling the electronic cassette 12 may be provided to the other housing section(s).

Figure 7:
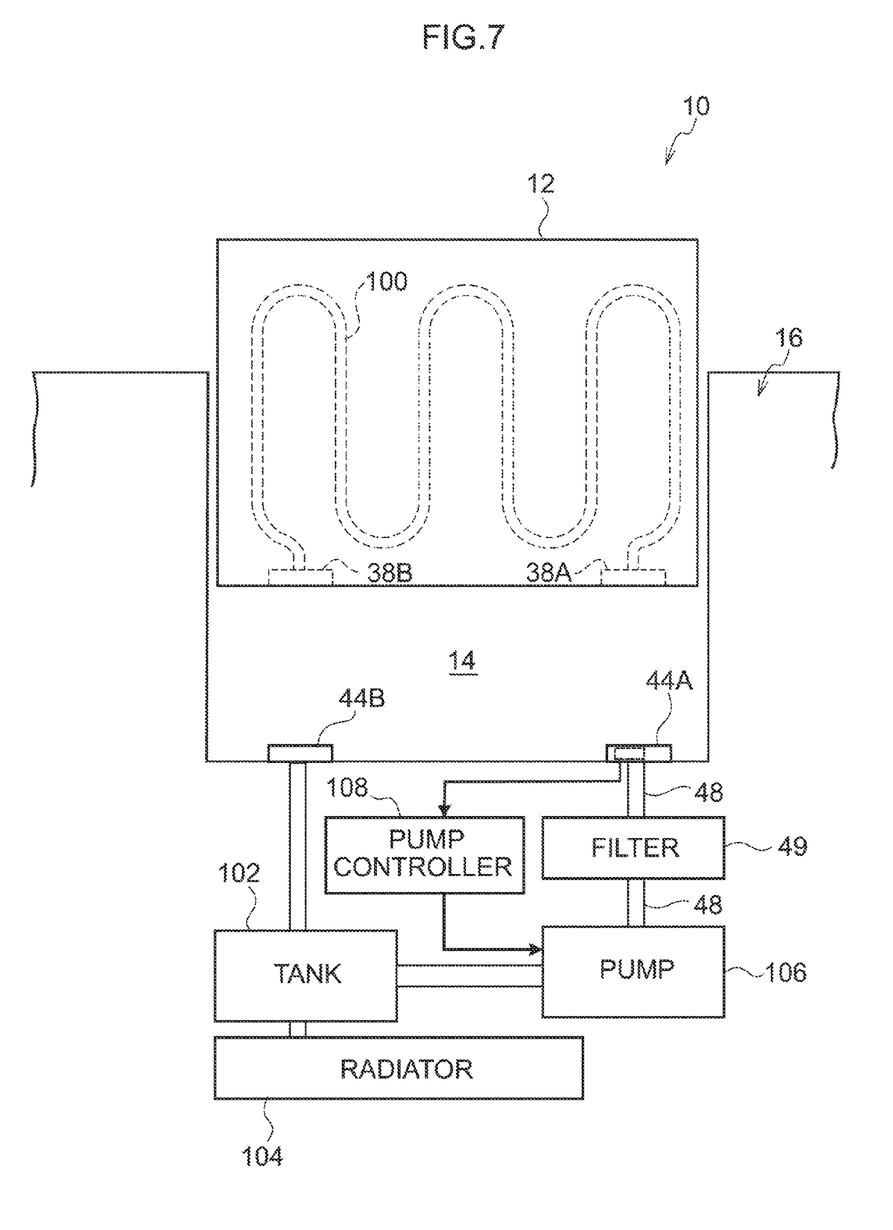
FIG. 7 is a cross-section view showing a configuration of an electronic cassette and a housing section according to another exemplary embodiment; of the present invention

While explanation has been given in the above exemplary embodiment of a case in which air is employed as the cooling medium for passing through inside the electronic cassette 12, there is no limitation thereto. Another gas, a liquid (for example water), or a powder (for example a thermo-memory) may be employed as the cooling medium. When a liquid or a powder is employed as the cooling medium to be passed through inside the electronic cassette 12, configuration may be made, for example as shown in FIG. 7, such that the electronic cassette 12 is provided with a flow port 38A for inflow of a liquid or powder and a flow port 38B for outflow of the supplied liquid or powder, in the side face 57 of the casing body 54. A pipe 100, acting as liquid or powder flow path, is disposed in a serpentine shape with plural bend inside the electronic cassette 12. Supply ports 44A, 44B are also provided to the housing section 14 in the prone image capture table 16, at positions aligned with the positions of the flow ports 38A, 38B when the electronic cassette 12 is in a housed state in the housing section 14. Also provided are: a tank 102 for holding the liquid or powder; a radiator 104 for cooling the liquid or powder held in the tank 102; a feed pump 106 for feeding the liquid or powder held in the tank 102 into the electronic cassette 12; and a pump controller 108 for controlling driving of the feed pump 106. When the electronic cassette 12 is housed in the housing section 14 and connection of the flow port 38A and the supply port 44A are detected by the contact detection sensor 46, the pump controller 108 of the prone image capture table 16 supplies the liquid or powder from the supply port 44A, circulates the liquid or powder inside the pipe 100 of the electronic cassette 12, thereby performing cooling. A filter 49 is also provided to the duct 48 connecting together the feed pump 106 and the supply port 44A in the configuration of FIG. 7, with incorporated foreign objects being removed by the filter 49.

Figure 8:
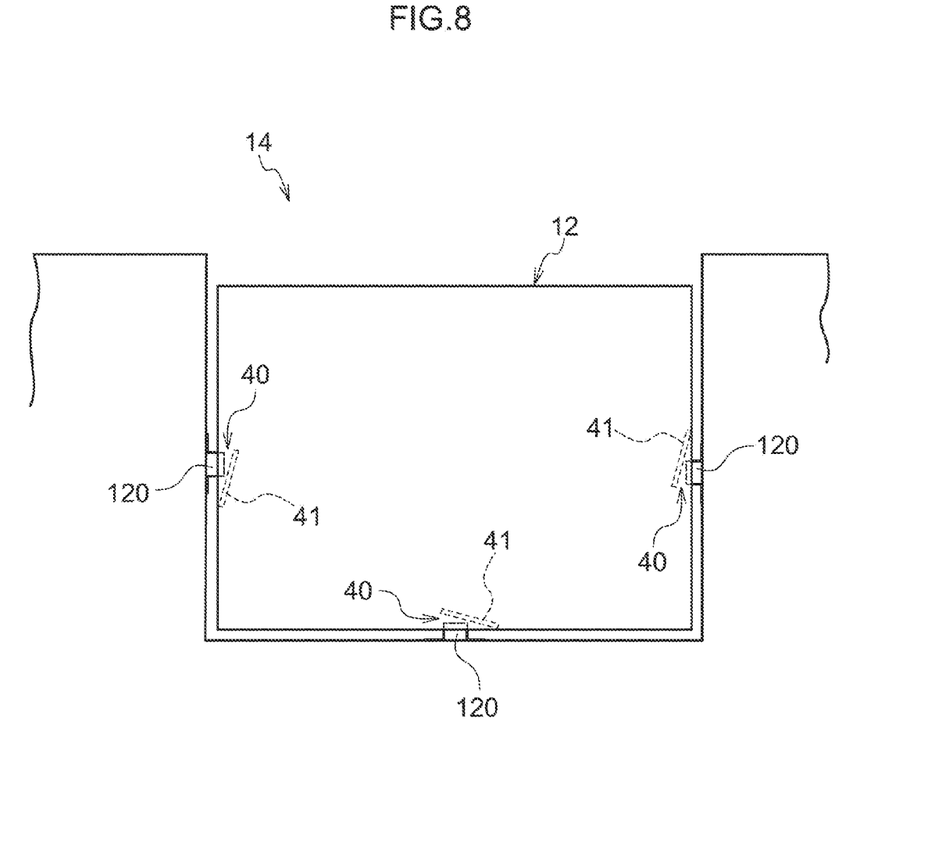
FIG. 8 is a cross-section view showing a configuration of an electronic cassette and a housing section according to another exemplary embodiment of the present invention.

While explanation has been given in the above exemplary embodiment of a case in which the opening and closing mechanism 42 for opening or closing the air passage ports 40 are provided to the electronic cassette 12, there is no limitation thereto. For example, configuration may be made such that the electronic cassette 12 is provided with lid members 41 closely sealed to each of the respective air passage ports 40, configured to be opened when pressed from outside, as shown in FIG. 8. The air passage ports 40 are then opened by being pressed by pressing members 120 capable of extending and retracting, such as solenoids, provided in positions on the housing section 14 of the prone image capture table 16 that are aligned with each of the respective air passage ports 40 when the electronic cassette 12 is in a housed state in the housing section 14. In such a configuration, the inside of the casing body 54 is also configured with a light blocking structure, such that light from each of the air passage ports 40 is blocked even when the air passage ports 40 are open, and the light blocking ability within the casing body 54 is maintained.

It should also be noted that the configurations of the electronic cassette 12 and the prone image capture table 16 in the above exemplary embodiments are merely examples thereof, and obviously appropriate modifications are possible within a scope not departing from the spirit of the present invention.

What is claimed is:

1. A radiographic image capture system comprising:
a portable radiographic image capture device comprising a sensor section that is sensitive to radiation or to light converted from radiation, an electronic circuit that controls capture of a radiographic image by the sensor section, and a casing that houses the sensor section and the electronic circuit and is provided with a flow port for flowing a cooling medium through from outside to inside; and
an image capture table comprising a housing section that houses the portable radiographic image capture device, and an inflow mechanism that flows the cooling medium into the flow port of the portable radiographic image capture device when housed in the housing section at least during the capture of the radiographic image.

2. The radiographic image capture system of claim 1, wherein the cooling medium is a gas, a liquid or a powder.

3. The radiographic image capture system of claim 1, wherein the inflow mechanism comprises a filter that removes foreign objects incorporated in the cooling medium, and the cooling medium is flowed into the flow port after passing through the filter.

4. The radiographic image capture system of claim 1, wherein the capture of the radiographic image is a fluoroscopic imaging.

5. A portable radiographic image capture device comprising:

a sensor section that is sensitive to radiation or to light converted from radiation;

an electronic circuit that controls capture of a radiographic image by the sensor section; and a casing that houses the sensor section and the electronic circuit and is provided with a flow port for flowing a cooling medium through from outside to inside at least during the capture of the radiographic image.

6. The portable radiographic image capture device of claim 5, wherein the capture of the radiographic image is a fluoroscopic imaging.

7. An image capture table comprising:

a housing section capable of housing a portable radiographic image capture device comprising a casing housing a sensor section that is sensitive to radiation or to light converted from radiation and an electronic circuit that controls capture of a radiographic image by the sensor section, the casing being provided with a flow port for flowing a cooling medium through from outside to inside; and an inflow mechanism that flows the cooling medium into the flow port of the portable radiographic image capture device when housed in the housing section at least during the capture of the radiographic image.

8. The image capture table of claim 7, wherein the capture of the radiographic image is a fluoroscopic imaging.

* * * * *